(12) United States Patent
Zhu

(10) Patent No.: US 10,894,110 B2
(45) Date of Patent: Jan. 19, 2021

(54) DEVELOPABLE HYALURONIC ACID MICROSPHERICAL EMBOLIC AGENT, PREPARATION METHOD AND USE THEREOF

(71) Applicant: Hangzhou Singclean Medical Products Co., Ltd., Zhejiang (CN)

(72) Inventor: Jianfeng Zhu, Zhejiang (CN)

(73) Assignee: Hangzhou Singclean Medical Products Co., Ltd., Hangzhou (CN)

( * ) Notice: Subject to any disclaimer, the term of this patent is extended or adjusted under 35 U.S.C. 154(b) by 0 days.

(21) Appl. No.: 16/258,663

(22) Filed: Jan. 27, 2019

(65) Prior Publication Data

US 2019/0231924 A1 Aug. 1, 2019

(30) Foreign Application Priority Data

Jan. 30, 2018 (CN) .......................... 2018 1 0088706

(51) Int. Cl.
| | | |
|---|---|---|
| *A61L 24/08* | (2006.01) | |
| *A61L 24/00* | (2006.01) | |
| *A61B 17/00* | (2006.01) | |
| *C08B 37/08* | (2006.01) | |
| *A61L 27/00* | (2006.01) | |
| *A61K 9/50* | (2006.01) | |
| *A61K 9/00* | (2006.01) | |
| *A61K 49/04* | (2006.01) | |
| *A61P 31/00* | (2006.01) | |

(52) U.S. Cl.
CPC .......... *A61L 24/08* (2013.01); *A61B 17/0057* (2013.01); *A61K 9/0024* (2013.01); *A61K 9/50* (2013.01); *A61K 9/5036* (2013.01); *A61L 24/001* (2013.01); *A61L 27/00* (2013.01); *A61P 31/00* (2018.01); *C08B 37/0072* (2013.01); *A61B 2017/0092* (2013.01); *A61B 2017/00526* (2013.01); *A61B 2017/00632* (2013.01); *A61K 49/0419* (2013.01); *A61K 49/0438* (2013.01); *A61L 2430/36* (2013.01)

(58) Field of Classification Search
CPC ........ A61B 17/12181; A61B 17/12186; A61B 17/1219; A61B 17/0057; A61L 27/20; A61L 27/52; A61L 27/54; A61L 2430/36; A61L 24/08; A61K 9/5161; A61K 9/1652; A61K 9/5036; A61K 49/0438
See application file for complete search history.

(56) References Cited

U.S. PATENT DOCUMENTS 7,094,369 B2 * 8/2006 Buiser .................. A61L 31/048
264/7

FOREIGN PATENT DOCUMENTS

| CN | 103450590 | * 12/2013 | ................ C08J 3/24 |
| WO | WO-2009077620 A1 | * 6/2009 | ............. A61K 8/025 |

OTHER PUBLICATIONS

Machine translation of CN 103450490. (Year: 2013).*
Thanoo, B. et al "Preparation and properties of barium sulphate . . . " J. Appl. Biomater., vol. 2, pp. 67-72. (Year: 1991).*

* cited by examiner

*Primary Examiner* — Leigh C Maier

(57) ABSTRACT

A developable hyaluronic acid microspherical embolic agent includes a hyaluronic acid and an X-ray opaque contrast material; wherein the hyaluronic acid is a modified hyaluronic acid, wherein a modifying method for preparing the modified hyaluronic acid is cross-linking, grafting, esterification, or recombination, and is preferably cross-linking.

10 Claims, 3 Drawing Sheets

DEVELOPABLE HYALURONIC ACID MICROSPHERICAL EMBOLIC AGENT, PREPARATION METHOD AND USE THEREOF

CROSS REFERENCE TO RELATED APPLICATION

This application claims priority to Chinese Patent Application No. 201810088706.6 filed on Jan. 30, 2018, the entire contents of which are incorporated herein by reference.

FIELD OF THE INVENTION

The present disclosure relates to a developable hyaluronic acid microspherical embolic agent and a preparation method thereof.

BACKGROUND OF THE INVENTION

Interventional embolization treatment refers to the delivery of an embolic drug through a catheter inserted into a target artery under X-ray fluoroscopic guidance to block blood supply to the tumor, thereby achieving an effect of physical embolization. This technique is most used in the treatment of liver cancer, and is much more advantageous over traditional chemotherapy.

At present, most of the clinically used embolic agent materials are X-ray translucent, and in practical use they need to be mixed with an X-ray opaque developing agent, such as barium sulfate, tantalum powder, etc. However, after the mixture is injected into a human body, the embolic agent and the developing agent could easily be separated from each other. This increases the risk of incorrect occlusion and misplacement of the embolus. Besides, after being injected into the human blood vessel, the developing agent flowing with the blood is soon metabolized in kidney and is excreted from the body. In this case, when a follow-up examination is conducted after the surgery, it is impossible to conduct an observation by using X-ray and a second imaging is thus needed, which will do more harm to the body of the patient.

Because of the above situation, it has become a main research direction of the field in recent years to prepare a new type of blood vessel embolic agent that is developable. One that is most studied at present is polyvinyl alcohol particle embolic agents, which are embedded therein with a developing agent such as tantalum powder, iodized oil, etc.; but these particles are not uniform in size and have no regular shapes, and can therefore easily lead to incomplete embolization. In recent years, microspherical embolic agents gradually replace traditional granular embolic agents. Microspherical embolic agents can better occlude distal blood vessels and can greatly decrease the coefficient of friction in the blood vessel during the embolization.

Hyaluronic acid was first discovered in the vitreous body of the cow's eye. It is a linear polymer polysaccharide composed of glucuronic acid and acetyl-glucosamine that link with each other. Natural hyaluronic acid can exist in a body for about three to fifteen days. Chemically modified hyaluronic acid has improved anti-degradation capability and retains the unique properties of hyaluronic acid such as biocompatibility, high viscoelasticity, and being free of side effect. An X-ray opaque hyaluronic acid microspherical embolic agent with smooth surface is prepared by emulsion polymerization during which a developing agent is embedded in the hyaluronic acid and the hyaluronic acid is chemically modified.

SUMMARY OF THE INVENTION

A first objective of the present disclosure is to provide a developable hyaluronic acid microspherical embolic agent. Spheres of the embolic agent have uniform forms and smooth surfaces, and are degradable and X-ray opaque. To achieve this objective, the present disclosure adopts the following technical solutions.

A developable hyaluronic acid microspherical embolic agent is provided. The developable hyaluronic acid microspherical embolic agent is composed of hyaluronic acid and an X-ray opaque contrast material. The X-ray opaque contrast material is embedded in the hyaluronic acid.

The hyaluronic acid is a modified hyaluronic acid. A modifying method may be cross-linking, grafting, esterification, or recombination, and is preferably cross-linking.

A second objective of the present disclosure is to provide a method of preparing a developable hyaluronic acid microspherical embolic agent. The method comprises the following steps:

1) preparing a hyaluronic acid solution having a concentration ranging from 0.1 g/mL to 0.3 g/mL, the solution containing an iodine compound;

2) adding the hyaluronic acid solution resulted from step 1) to a liquid paraffin containing an emulsifying agent, and emulsifying the resultant mixture with a shearing machine at a speed ranging from 500 rpm to 2000 rmp, to produce a water-in-oil emulsion, including hyaluronic acid microspheres in which the iodine compound is embedded;

3) adding 0.2-2 vol % of a cross-linking agent to the emulsion resulted from step 2), stirring the emulsion at room temperature for 4-6 hours for cross-linking reaction, keeping the emulsion still after the reaction finishes to form an oil phase layer and a aqueous phase layer, removing the oil phase layer, then washing the aqueous phase layer orderly with an acid solvent and a water-soluble organic solvent, and finally vacuum drying the aqueous phase layer to obtain hyaluronic acid microspheres containing the iodine compound, the microspheres being developable under an X-ray machine.

The X-ray opaque contrast material may be a water soluble iodine compound, and is preferably sodium iodide which is an inorganic iodide compound, or a nonionic iodide compound with low toxic side effect selected from organic iodine compounds. The nonionic iodide compound with low toxic side effect may be selected from a group consisting of N,N'-bis(2,3-dihydroxypropyl)-2,4,6-triiodo-5-[(2-methoxyacetyl)amino]-N'-methylbenzene-1,3-carboxamide (iopromide), N,N'-bis(2,3-dihydroxypropyl)-5-[N-(2,3-dihydroxypropyl)acetamino]-2,4,6-triiodois ophthalamide (iohexol), (S)—N,N'-bis[2-hydroxy-1-(hydroxymethyl)ethyl]-5-[N-[(2-hydroxy-1-oxopropyl)amino]-2,4,6-triiodo-1,3-benzenedicarboxamide (iopamidol), and 5,5'-((2-hydroxy-1,3-propane)bis(acetylimino))bis(N,N'-bis(2,3-dihydroxypropyl)-2,4, 6-triiodo-1,3-benzenedicarboxamide (iodixanol).

Preferably, the hyaluronic acid is a sodium hyaluronate produced by bacterial fermentation. This eliminates animal derived risk that can be brought by the extraction from animals. In order to improve the yield of the microspheres, the sodium hyaluronate has a molecular weight ranging from 0.3 million to 3 million dalton, preferably ranging from 0.6 million to 2 million dalton.

The hyaluronic acid solution is alkaline, and is preferably prepared from sodium hydroxide solution.

The cross-linking agent may be selected from the group consisting of epoxides, divinyl sulphone, 1,4-butanediol diglycidyl ether, and diglycidyl ether, and is preferably 1,4-butanediol diglycidyl ether which has a low toxic side effect.

The emulsifying agent may be selected from spans, or one or more from the combinations of spans and tweens.

The developable hyaluronic acid microspheres have a particle size ranging from 80 μm to 2000 μm after being redissolved in normal saline or in a phosphate buffer.

The acid solvent is preferably acetic acid. The water soluble organic solvent is preferably ethyl acetate, absolute ethanol, or acetone. The acid solvent is used primarily to adjust the pH value of the aqueous phase layer and to prevent the cross-linking reaction, so as to avoid a too high cross-linking degree that will affect the efficiency of embedding the developing agent material. The water soluble solvent is used mainly for washing away the residual oil phase.

The developable hyaluronic acid microspherical embolic agent may be used in conjunction with an anti-cancer drug, and may serve as an embolic agent after being loaded with the drug. Further, the developable hyaluronic acid microspherical embolic agent may be useful in the preparation of drugs for arterial embolization and local targeted embolization treatment for endometrial cancer, lung cancer, liver cancer, kidney cancer, angiomas, and various vascular solid visceral tumors.

The present disclosure is advantageous in that the developable hyaluronic acid microspherical embolic agent retains the good biocompatibility of the hyaluronic acid, and the hyaluronic acid is produced by bacterial fermentation, which avoids animal derived risks and clinic safety is thus ensured. Besides, the microspheres have uniform forms and smooth surfaces, which can improve the embolization effect in clinic practice. The capability of the embolic agent to develop can remarkably improve the success rate of the embolization, reduce the use of embolization materials and developing agents, and thus enormously decrease toxic side effects. Furthermore, the developable hyaluronic acid microspherical embolic agent is degradable in a body, and can be prepared to contain an anti-cancer drug, by way of which it may have a role not only in the embolization but also in targeted chemotherapy.

DETAILED DESCRIPTION OF THE EMBODIMENTS

Figure 1A:
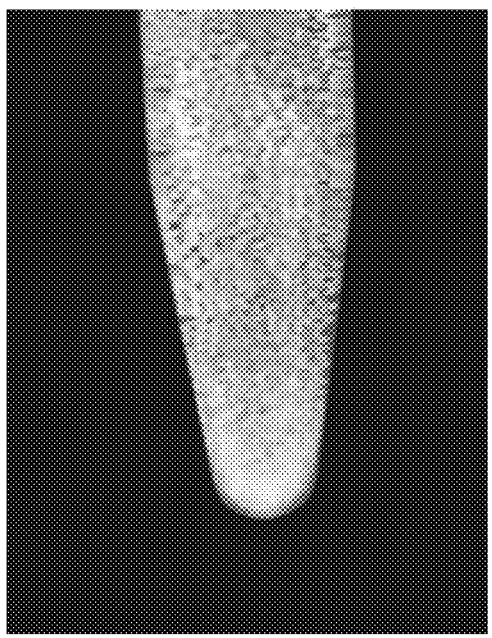
FIG. 1A and FIG. 1B show development effects of the product prepared according to example 1 (FIG. 1A) and a positive control (FIG. 1B) under X-ray radiation.

Examples will be provided below to explain the present disclosure in more detail, but the present disclosure is not limited thereto.

Example 1: Preparation of Hyaluronic Acid Microspherical Embolic Agent Containing Iohexol A hyaluronic acid solution having a concentration of 0.1 g/mL was prepared by using 8.04 g of solid power of sodium hyaluronate and 0.5% of sodium hydroxide solution. The hyaluronic acid solution contained 0.07 g/mL of iohexol. The hyaluronic acid solution was added to an oil phase containing 200.71 g of liquid paraffin and 3.41 g of Span 80. The resultant mixed phase was emulsified and dispersed for 10 minutes by using a shearing machine at 1000 rpm, to obtain a water-in-oil hyaluronic acid microspheres emulsion. 1% of 1,4-butanediol diglycidyl ether was added to the emulsion and the resultant mixture was stirred for 4 hours at room temperature for cross-linking reaction. After the stirring was finished, the mixture was kept still overnight to leave the microspheres to settle. The oil phase at the upper layer was poured away, and then acetic acid was added to adjust the pH value of the remaining mixture to be in a range of from 4.0 to 5.0. After that, the remaining mixture was washed in turn with ethyl acetate and absolute ethanol to remove the residual organic phase, and then dried in vacuum to obtain sodium hyaluronate microspheres containing the iodine compound. At last, the microspheres were sieved and sterilized to obtain a developable hyaluronic acid microspherical embolic agent.

Example 2: Preparation of Hyaluronic Acid Microspherical Embolic Agent Containing Iohexol A hyaluronic acid solution having a concentration of 0.1 g/mL was prepared by using 8.02 g of solid power of sodium hyaluronate and 0.5% of sodium hydroxide solution. The hyaluronic acid solution contained 0.07 g/mL of iohexol. The hyaluronic acid solution was added to an oil phase containing 201.01 g of liquid paraffin and 3.45 g of Span 80. The resultant mixed phase was emulsified and dispersed for 10 minutes by using a shearing machine at 1000 rpm, to obtain a water-in-oil hyaluronic acid microspheres emulsion. 1% of 1,4-butanediol diglycidyl ether was then added to the emulsion and the resultant mixture was stirred for 4 hours at room temperature for cross-linking reaction. After the stirring was finished, the mixture was kept still overnight to leave the microspheres to settle. The oil phase at the upper layer was poured away, and the remaining mixture was washed in turn with ethyl acetate and absolute ethanol to remove the residual organic phase, and then vacuum dried to obtain sodium hyaluronate microspheres containing the iodine compound. At last, the microspheres were sieved and sterilized to obtain a developable hyaluronic acid microspherical embolic agent.

Measurement of Content of Developing Agent in Hyaluronic Acid Microspherical Embolic Agent Dried microspheres prepared according to the above examples were respectively taken and dissolved in normal saline. After the microspheres were well swollen, the content of the developing agent in the microspheres was measured. The content of iohexol was measured by ultraviolet spectrophotometry.

The content of iohexol in the microspheres prepared in example 1 was 26%.

The content of iohexol in the microspheres prepared in example 2 was 18%.

Test of Development Effect of Hyaluronic Acid Microspherical Embolic Agent

The hyaluronic acid microspherical embolic agent prepared in example 1 was taken to mix with 1 mL of normal saline. 1 mL of iohexol was measured out separately to be used as a positive control. Development test was carried out under an X-ray machine.

Comparative Example 1: Preparation of Cross-Linked Hyaluronic Acid Microspherical Embolic Agent Free of Developing Material A hyaluronic acid solution having a concentration of 0.1 g/mL was prepared by using 8.14 g of solid power of sodium hyaluronate and 0.5% of sodium hydroxide solution. The solution was added to an oil phase containing 200.98 g of liquid paraffin and 3.42 g of Span 80. The resultant mixed phase was emulsified and dispersed for 10 minutes by using a shearing machine at 1000 rpm, to obtain a water-in-oil hyaluronic acid microspheres emulsion. 1% of 1,4-butanediol diglycidyl ether was then added to the emulsion and the resultant mixture was stirred for 4 hours at room temperature for cross-linking reaction. After the stirring was finished, the mixture was kept still overnight to leave the microspheres to settle. The oil phase at the upper layer was poured away, and then the remaining mixture was washed in turn with ethyl acetate and absolute ethanol to remove the residual organic phase. The resulted mixture was then vacuum dried to obtain sodium hyaluronate microspheres containing the iodine compound. At last, the microspheres were sieved and sterilized to obtain a developable hyaluronic acid microspherical embolic agent.

Figure 1B:
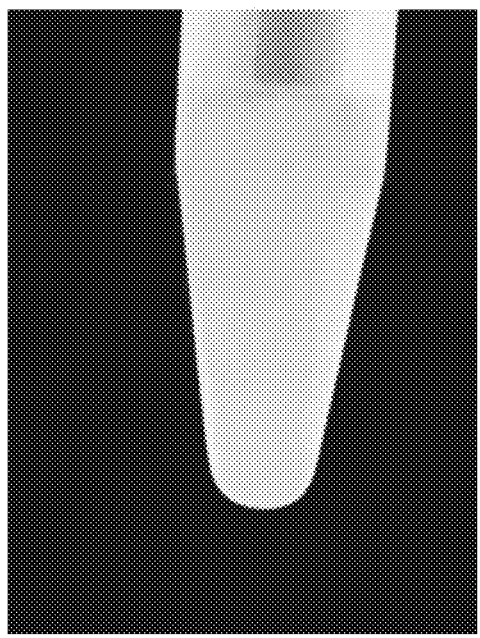

FIG. 1A shows the development effects of the product prepared according to example 1 under X-ray radiation, and FIG. 1B shows the development effects of a positive control (product in comparative example 1).

Test Example 1: Property Test of Hyaluronic Acid Microspherical Embolic Agent Embedded with a Developing Agent Samples prepared in the examples and the comparative example were subjected to tests on compression deformation property, swelling degree, and content of sodium hyaluronate, to assess whether or not the samples embedded with the developing agent still retained their original properties. The compression deformation property represents the elasticity of the microspheres. Good compression deformation property allows the embolic microspheres to deform effectively in order to pass through an injector and a microcatheter and then return to their original states. Swelling degree represents the cross-linking degree of the microspheres, which is manifested in the degradability of the microspheres in vivo. The content of sodium hyaluronate represents the effective component of the embolic microspheres, and it was determined by carbazole method.

Figure 2:
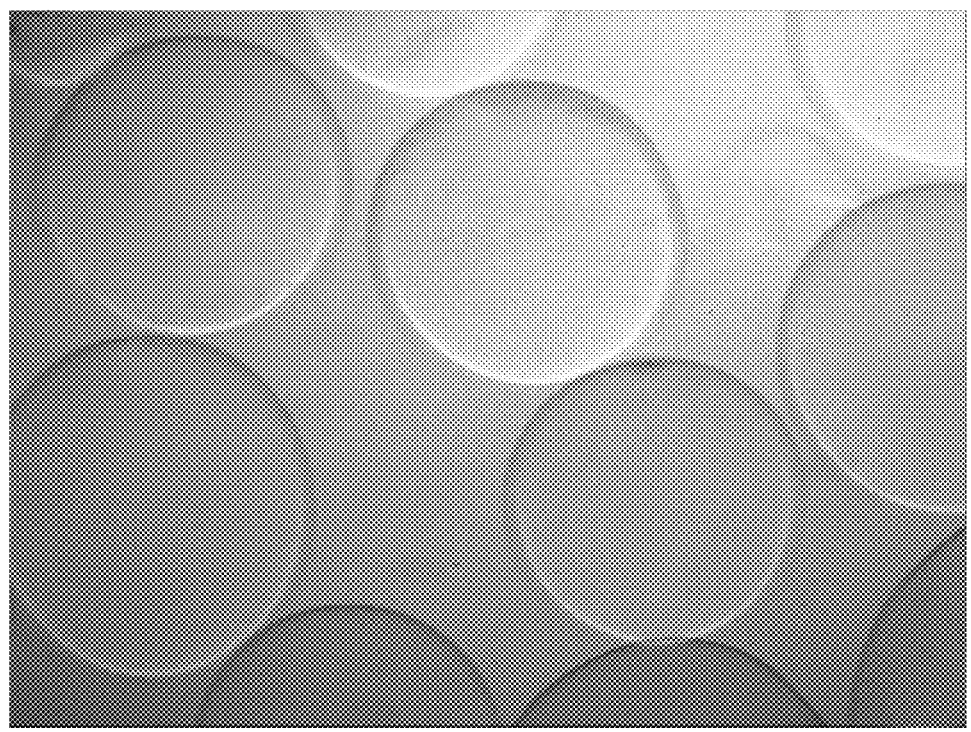
FIG. 2 is a view of the product prepared according to example 1 under a scanning electron microscope, in which microspheres have uniform shapes and smooth surfaces.
Figure 3A:
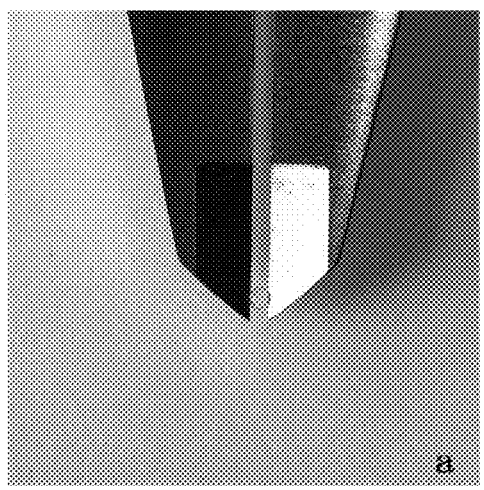
FIG. 3A and FIG. 3B show a comparison of the product prepared according to example 1 before (FIG. 3A) and after (FIG. 3B) the product is compressed to deform.
Figure 3B:
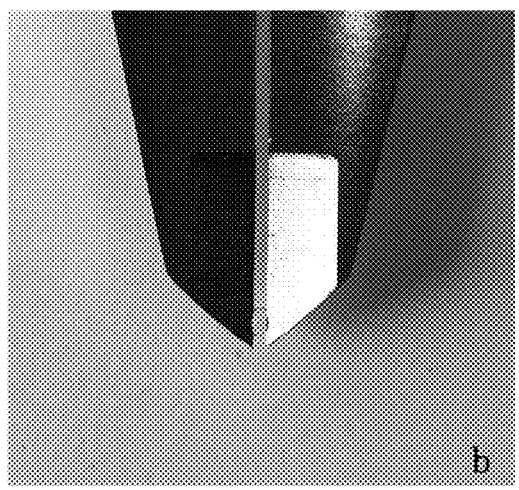

As shown in FIG. 2, the product prepared in example 1 includes microspheres having uniform shapes and smooth surfaces. FIGS. 3A and 3B shows a comparison of the product prepared according to example 1 before (FIG. 3A) and after (FIG. 3B) the product is compressed to deform.

| Property Test | Example 1 | Example 2 | Comparative Example 1 |
|---|---|---|---|
| Compression Deformation | 62.4% | 44.2% | 59.7% |
| Swelling Degree | 96 | 68 | 90 |
| Content of Sodium Hyaluronate | 12.5 mg/mL | 16.2 mg/mL | 13.4 mg/mL |

A comparison between the determined contents of the developing agents of example 1 and example 2 shows that, with other preparation procedures being the same, according to the method of the present disclosure, the use of an acid solvent to wash the microspheres obtained after the cross-linking reaction to decrease the pH value of the environment can lead to microspheres with a higher content of the developing agent and a better embedding efficiency, as compared to directly using a water soluble organic solvent to wash the microspheres obtained after the cross-linking reaction.

A comparison between example 1 and comparative example 1 shows that, with the feed ratio and process parameters being the same, a procedure of embedding a developing agent material was added in example 1, but the results of the property tests of the microsherical embolic agents prepared in example 1 and comparative example 1 are basically the same.

The above examples are only specific examples of the present disclosure, and features of the present disclosure are not limited thereto. Any variations or modifications in the field of the present disclosure made by any person skilled in the art shall fall within the protection scope of the present disclosure.

What is claimed is:

1. A method of preparing a developable hyaluronic acid microspherical embolic agent, wherein the method comprises the following steps:
    1) preparing a hyaluronic acid solution having a concentration ranging from 0.1 g/mL to 0.3 g/mL, wherein the solution contains an iodine compound;
    2) adding the hyaluronic acid solution resulted from step 1) to a liquid paraffin containing an emulsifying agent, and emulsifying with a shearing machine at a speed ranging from 500 rpm to 2000 rmp, to produce a water-in-oil emulsion comprising hyaluronic acid microspheres embedded with the iodine compound;
    3) adding 0.2-2 vol% of a cross-linking agent to the emulsion resulted from step 2), stirring the emulsion at room temperature for 4-6 hours for cross-linking reaction, keeping the emulsion still after the reaction is finished to form an oil phase layer and an aqueous phase layer, removing the oil phase layer, then washing the aqueous phase layer orderly with an acid solvent and a water soluble organic solvent, and vacuum drying the aqueous phase layer to obtain hyaluronic acid microspheres containing the iodine compound, wherein the microspheres are the hyaluronic acid microspherical embolic agents developable under an X-ray machine.

2. The method of preparing the developable hyaluronic acid microspherical embolic agent according to claim 1, wherein: the hyaluronic acid is sodium hyaluronate produced by bacterial fermentation and has a molecular weight ranging from 0.3 million to 3 million dalton; the cross-linking agent is one selected from the group consisting of epoxides, divinyl sulphone, 1,4-butanediol diglycidyl ether, and diglycidyl ether; and the emulsifying agent is sorbitan oleate, or polyoxyethylene (20) sorbitan monooleate, or one or more from the combinations of sorbitan oleate and polyoxyethylene (20) sorbitan monooleate.

3. The method of claim 1, wherein the washing with the acid solvent in step 3) lowers the pH value of the aqueous phase layer to about 4.0 to 5.0.

4. The method of claim 1, wherein the aqueous phase layer after being washed with the acid solvent, is washed in turn with ethyl acetate and absolute ethanol.

5. The method of claim 1, wherein the iodine compound is one selected from the group consisting of sodium iodide, N,N$^{40}$-bis(2,3-dihydroxypropyl)-2,4,6-triiodo-5-[(2-methoxyacetyl)amino ]-N'-methylbenzene-1,3 -carboxamide (iopromide), N,N'-bis(2,3-dihydroxypropyl)-5-[N-(2,3-dihydroxypropyl) acetamino]-2,4,6-triiodoisophthalamide (iohexol), (S)-N,N'-bis[2-hydroxy-1-(hydroxymethy) ethyl]-5-[N-[(2-hydroxy-1-oxopropyl)amino ]-2,4,6-triiodo-1,3-benzenedicarboxamide(iopamidol), and 5,5'-((2-hydroxy-1,3-propane)bis (acetylimino))bis(N,N-bis(2,3-dihydroxypropyl)-2,4,6-triiodo-1,3-benzenedicarboxamide (iodixanol).

6. The method of claim 4, wherein the acid solvent is acetic acid.

7. The method of claim 4, wherein the water soluble organic solvent is one selected from the group consisting of ethyl acetate, absolute ethanol, and acetone.

8. The method of claim 4, wherein 1) the hyaluronic acid is sodium hyaluronate produced by bacterial fermentation and has a molecular weight ranging from 0.3 million to 3 million Dalton; 2) the iodine compound is iohexol; 3) the emulsifying agent is sorbitan oleate; 4) the cross-linking agent is 1,4-butanediol diglycidyl ether;

5) the acid solvent is acetic acid; and 6) the water soluble organic solvent is ethyl acetate and absolute ethanol.

9. A method of preparing a developable hyaluronic acid microspherical embolic agent, wherein the method comprises the following steps:

1) preparing a hyaluronic acid in sodium hydroxide solution having a concentration of about 0.1 g/mL, wherein the solution contains 0.07 g/mL of iohexol;

2) adding the hyaluronic acid solution resulted from step 1) to a liquid paraffin containing about 200-205g of liquid paraffin and about 3.0 to 4.0g sorbitan oleate, and emulsifying with a shearing machine at a speed ranging from 500 rpm to 2000 rmp, to produce a water-in-oil emulsion comprising hyaluronic acid microspheres embedded with iohexol;

3) adding about 1% of 1,4-butanediol diglycidyl ether to the emulsion resulted from step 2), stirring the emulsion at room temperature for 4-6 hours for cross-linking reaction, keeping the emulsion still after the reaction is finished to form an oil phase layer and an aqueous phase layer, removing the oil phase layer, then washing the aqueous phase layer orderly with an acetic acid and in turn with ethyl acetate and absolute ethanol, and vacuum drying the aqueous phase layer to obtain hyaluronic acid microspheres containing iohexol, wherein the microspheres are hyaluronic acid microspherical embolic agents developable under an X-ray machine.

10. The method of claim 9, wherein the hyaluronic acid is sodium hyaluronate produced by bacterial fermentation and has a molecular weight ranging from 0.3 million to 3 million Dalton.

* * * * *